United States Patent [19]

Mc Venes et al.

[11] Patent Number: 5,741,311
[45] Date of Patent: Apr. 21, 1998

[54] IMPLANTABLE MEDICAL DEVICE SYSTEM WITH METHOD FOR DETERMINING LEAD CONDITION

[75] Inventors: Rick D. Mc Venes, Isanti; Brent A. Bahr, Big Lake; Terrence R. Hudrlik, Blaine, all of Minn.

[73] Assignee: Medtronic, Inc., Minneapolis, Minn.

[21] Appl. No.: 671,437

[22] Filed: Jun. 27, 1996

[51] Int. Cl.⁶ .................................................. A61N 1/37
[52] U.S. Cl. .................................................. 607/28
[58] Field of Search .......................... 607/8, 11, 27, 607/28

[56] References Cited

U.S. PATENT DOCUMENTS

| | | |
|---|---|---|
| 4,805,621 | 2/1989 | Heinze et al. |
| 4,899,750 | 2/1990 | Ekwall ............................... 607/28 |
| 4,964,407 | 10/1990 | Baker, Jr. et al. |
| 5,003,975 | 4/1991 | Hafelfinger et al. |
| 5,201,865 | 4/1993 | Kuehn ............................... 607/28 |
| 5,233,986 | 8/1993 | Robson ............................... 607/27 |
| 5,318,593 | 6/1994 | Duggan. |

OTHER PUBLICATIONS

Pending Patent Application, Wahlstrand et al., "Automatic Lead Recognition For Implantable Medical Device," U.S. application Ser. No. 08/346,661, filed Nov. 30, 1994.

Primary Examiner—Marvin M. Lateef
Assistant Examiner—George R. Evanisko
Attorney, Agent, or Firm—Michael J. Jaro; Harold Patton

[57] ABSTRACT

In an implantable medical device system such as a pacemaker system, there is provided a system and method for measuring lead impedance so as to obtain reliable data concerning any indication of the need to replace the lead. A relatively short duration low current AC burst is delivered after a standard pacing pulse, at a time to coincide with the heart's refractory period. The pulse is long enough in duration, e.g., 50–125 ms and preferably around 100 ms, to achieve the benefit of substantially steady state measurement, but short enough to substantially avoid the possibility of inducing any cardiac arrhythmia. The current level of the burst is limited to about 30 microamps, providing a further factor of safety against inducing an unwanted arrhythmia. The PPAC technique is adaptable for automatic measurement within an implantable device, or for implementation involving an external programmer which triggers the test.

17 Claims, 3 Drawing Sheets

IMPLANTABLE MEDICAL DEVICE SYSTEM WITH METHOD FOR DETERMINING LEAD CONDITION

FIELD OF THE INVENTION

This invention relates generally to the field of implantable medical device systems and, more particularly, to implantable pacemaker systems incorporating a lead interconnecting between a pacemaker and the patient's heart, and incorporating a feature for safely and reliably testing the lead condition.

BACKGROUND OF THE INVENTION

A wide assortment of automatic, body-implantable medical devices are presently known and in commercial use. Such devices include cardiac pacemakers, cardiac defibrillators, cardioverters, neurostimulators, and other devices for delivering electrical signals to a portion of the body and/or receiving signals from the body. Pacemakers, for example, are designed to operate so as to deliver appropriately timed electric stimulation signals when needed, in order to cause the myocardium to contract or beat, and to sense naturally occurring conduction signals in the patient's heart.

Devices such as pacemakers, whether implantable or temporary external type devices, are part of a system for interacting with the patient. In addition to the pacemaker device which typically has some form of pulse generator, a pacing system comprises one or more leads for delivering the generated signals to the heart and for sensing and delivering sensed signals from the heart back to the pacemaker. As is known, pacemakers can operate in either a unipolar or bipolar mode, and can pace the atria or the ventricles. Unipolar pacing requires a lead having only one distal electrode for positioning in the heart, and utilizes the case, or housing of the implanted device as the other electrode for the pacing and sensing operations. For bipolar pacing and sensing, the lead typically has two electrodes, one disposed substantially at the distal tip end of the lead, and the other spaced somewhat back from the distal end. For a dual chamber pacemaker, one such lead is positioned in the patient's ventricle and another in the patient's atrium. Pacemaker systems, as well as other medical devices as such mentioned above, can utilize a wide variety of lead designs, as is well documented in the patent literature.

The problem addressed by this invention is that of determining when a lead may be approaching a condition where a replacement is indicated. As is known, leads that are implanted within a patient have an intended lifetime of years, during which they undergo repeated flexing and stressing. While the state of the art has produced significant advances which have lead to substantial increases in reliability, the potential for lead failure has not been eliminated. One of the conductors, or one of the electrodes on an implanted lead can fail for a number of reasons, e.g., breakage of a conductor due to metal fatigue, poor connections between the lead and the pacemaker itself, tissue degradation at the electrode site, subclavian crushing of the lead, metal ion oxidation, or shorting of the lead conductors due to insulation breakdown. Lead studies have shown that low resistance failures of leads can sometimes be seen clinically, such as by a manifestation of oversensing, or noise pick-up. It is our understanding that in the early stages of lead failure, the lead may not be in a low resistance (impedance) steady state condition, i.e., the low resistance may be only intermittent. For this reason, detection of the failure may not be detected early by standard pacing pulse delivery and resistance measures. A pacing pulse is typically only about 0.5 to 1.0 ms duration, which can be too short to accurately detect lead failure. However, delivery of an AC current through the lead should drive the system to a steady state condition where lead failure can be found. A problem with continuous AC impedance measurement, however, is the potential for introducing either atrial or ventricular fibrillation. There remains a need in the art, and particularly the pacemaker art, for a lead elective replacement indictor (ERI) which is reliable, which can give a sufficiently early indication, and which does not have any detrimental side effects, particularly as concerns inducing cardiac arrhythmias.

SUMMARY OF THE INVENTION

It is an object of the invention to provide, for an implantable system having a lead subject to high or low impedance failure, and especially low impedance failure, a capability of testing the lead so as to determine when elective replacement is indicated. The invention meets the need of sensing lead failure at an early stage where the lead is still operative but may be manifesting signs of intermittent low impedance, while avoiding the potential dangers of inducing arrhythmias as have been associated with prior art lead measurement techniques.

The system and method of this invention provide for delivery of a post-stimulus pulse AC (PPAC) burst of a current within a predetermined current range, and for a duration which is long enough to provide substantially steady state test conditions. In the pacemaker embodiment, the measuring burst is timed to follow delivery of a stimulus pulse, so that it comes during the refractory period of the cardiac muscle, thereby essentially removing the danger of initiating any unwanted arrhythmia. The measuring burst, on the order of about 100 ms, is long enough to drive the lead into a state of equilibrium so as to get a valid impedance determination, but short enough to provide more than an order of magnitude protection for arrhythmia induction compared to delivery of a continuous wave AC signal at the same level.

DESCRIPTION OF THE PREFERRED EMBODIMENTS

Figure 1:
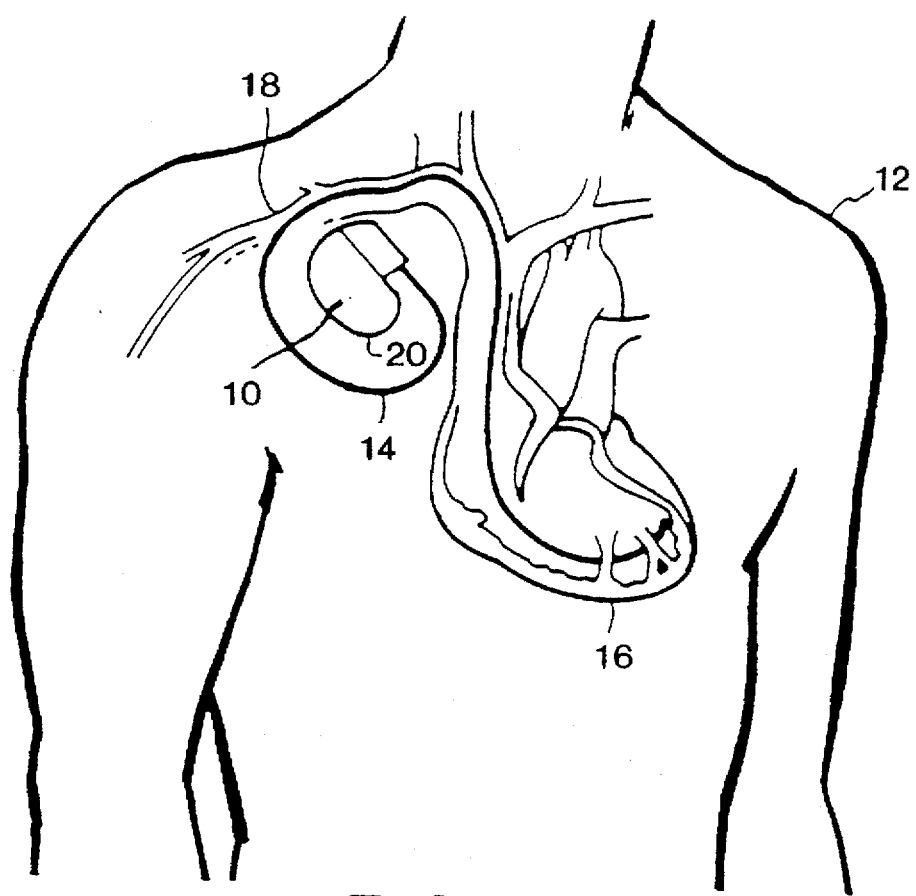
FIG. 1 is a schematic representation of an implanted pacemaker system, illustrating an implantable pacemaker and the lead interconnecting the patient's heart and the pacemaker.

Referring now to FIG. 1, there is shown an illustration of a pacemaker 10, as an exemplary implantable device, implanted in a patient 12. In accordance with conventional practice in the art, pacemaker 10 is housed within a hermetically sealed, biologically inert canister 20, which is suitably conductive and thus serves as an indifferent electrode in the pacemaker system.

One or more pacemaker leads, collectively identified with the reference numeral 14 are electrically coupled to pacemaker 10 in a conventional manner, and extend into the patient's heart 16 via vein 18. Disposed generally near the distal end of the lead 14 are one or more exposed conductive electrodes for receiving electrical cardiac signals and/or for delivering electrical pacing stimuli to the patient's heart. Although illustrated with the distal end of the lead in the patient's ventricle, the distal end may be situated in the atrium or the ventricle for a single chamber pacemaker, or there may be leads in both atrium and ventricle for a dual chamber-type pacemaker.

Figure 2A:
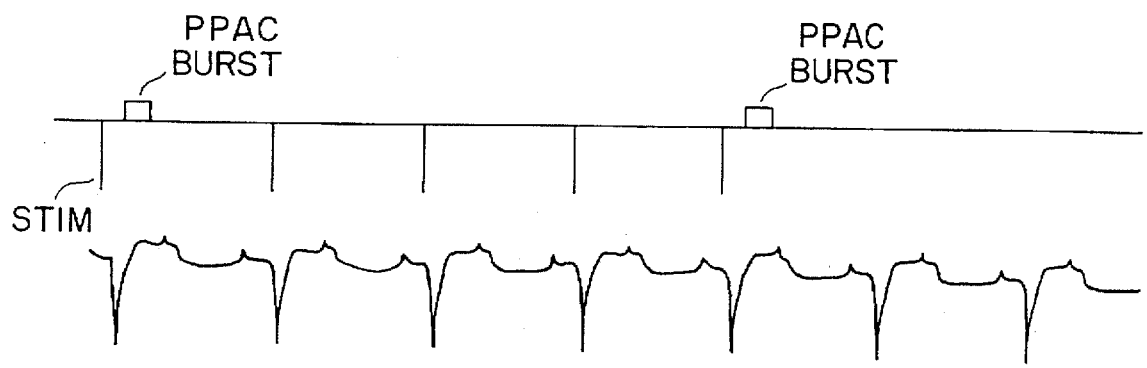
FIG. 2A is a drawing illustrating the timing relation of the post-pulse AC burst with respect to a delivered stimulus pulse.
Figure 2B:
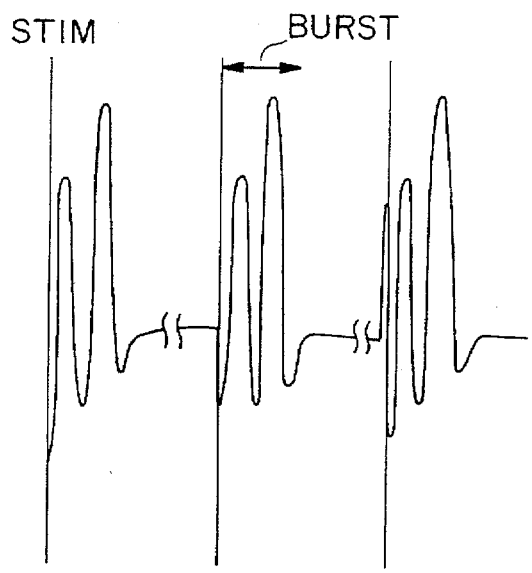
FIG. 2B is a drawing showing a PPAC burst triggered by a delivered stimulus pulse.

Referring now to FIG. 2A, there are shown two curves illustrating the timing of delivering a PPAC burst to the patient. The lower curve is a representative ECG signal, showing the relatively large downward QRS wave which is evoked in response to a delivered stimulus beat. The QRS wave is followed by the T wave, and then, as is known, a next succeeding P wave is detected from the atrium, prior to a next succeeding ventricular QRS. The PPAC is illustrated in the upper timing diagram as being triggered just after the delivery of the stimulus pulse, and extending for a time period of about 100 ms, e.g., 100±10 ms. The short duration burst is timed to be delivered while the heart is refractory due to the contraction. The time interval between delivery of the relatively short stimulus (on the order of 1 ms) and the initiation of the PPAC burst is typically in the range of 0.1–10 ms, although the burst may be triggered directly by the stimulus pulse. FIG. 2B illustrates a 20 Hz burst of 100 ms duration, which is triggered by the pace pulse.

Figure 3:
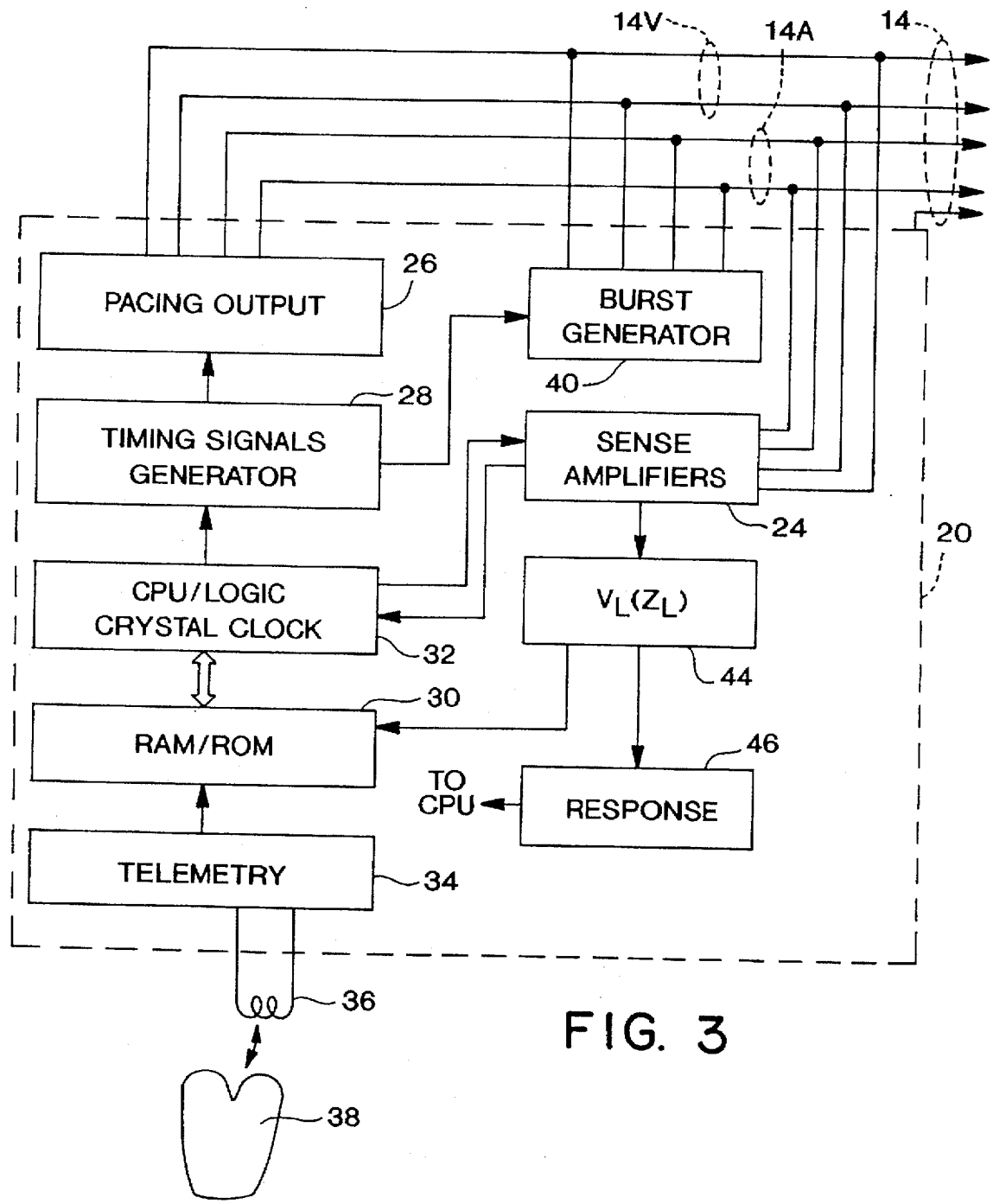
FIG. 3 is a block diagram of a pacemaker incorporating the feature of this invention, illustrating the primary components used to provide post-pulse AC capability.

Referring now to FIG. 3, there is shown a block diagram of a pacemaker 20 in accordance with this invention. It will be recognized that only the primary components are set forth, in order to simplify explanation of the improvement incorporated. The components are standard components used in pacemakers and other medical devices, the details of which are well understood in the art.

The pacemaker 20 is interconnected with the patient by lead 14, which is illustrated as comprising five respective conductors connected to a tip electrode position in the ventricle (VTIP); a ring electrode position in the ventricle (VRING); a tip electrode in the atrium (ATIP); a ring electrode in the atrium (ARING); and the pacemaker case, which is suitably system ground. A pacing output circuit 26 generates stimulus pulses which are connected to or across one or more of the illustrated lead conductors depending upon the pacemaker configuration and mode. The pacing output pulses are controlled in terms of timing and duration by a timing signals generator 28, which in turn is controlled by CPU/logic block 32. CPU/logic block 32 also contains a crystal clock for driving appropriate timing generators and/ or controlling timing signals outputted by the microprocessor of the CPU, in a known fashion. CPU block 32 is interconnected with appropriate RAM/ROM memory 30. A telemetry circuit 34, having a receiver unit 36, interfaces with an external programmer 38, and provides programming data to the memory 30.

Still referring to FIG. 3, a burst generator 40 is shown having outputs switchably connected to the respective lead lines, and receiving timing signals from generator 28. In the practice of this invention, following delivery of a trigger signal to the pacing output 26, a predetermined number of milliseconds later a timing signal is transmitted to burst generator 40, which controls the initiation and duration of the PPAC burst. Burst generator 40 is suitably a 10 volt peak-to-peak AC generator, in series with approximately 330K, to provide a 30 microamp peak-to-peak constant current burst. Of course, any convention circuit design may be employed. The duration of the burst is controlled to a time in the range of about 50–125 ms. The longer the burst duration, the better stabilized the impedance measurement, but burst duration is necessarily limited for the safety reasons that have been set forth above. The frequency of the PPAC is suitably in the range of about 10–1000 Hz, for best results. The peak-to-peak current value is suitably 30 microamps or less, to provide a large factor of safety against inducing fibrillation or any other arrhythmia. Of course, in some circumstances it may be found that the current can be safely increased, and while a peak-to-peak current of 30 microamps or less is deemed to be critical for extremely reliable operation, greater currents are within the scope of the invention.

When the PPAC is delivered by the burst generator, the voltage occurring across the leads is dependent primarily upon the impedance of the lead. Since the impedance is very large for a lead that is in satisfactory condition, the impedance presented by the patient's heart tissue is negligible. Consequently, since the burst generator delivers a constant current signal, the voltage seen at sense amplifier 24 is a function of the lead impedance. This voltage, represented as $V_L$, is measured by voltage detector 44, and the resulting value is suitably stored in memory. Additionally, a response means 46 may be provided, preferably in the form of software associated with the CPU, for analyzing the $V_L$ measurement and the history of $V_L$ and initiating an appropriate pacemaker response in the event that replacement is indicated.

For an implanted pacemaker, the software may be provided with a routine for causing generation of a PPAC on a periodic basis, e.g., once an hour or once a day, with consequent storage of the $V_L$ data and/or automatic response if indicated. In another embodiment, the PPAC may be utilized during a programming sequence by the physician. Thus, for a conventional external programmer application which goes into a predetermined routine, the pacemaker is suitably placed in an asynchronous fixed rate mode, and the PPAC can be programmed by programmer 38 to be delivered as one or more bursts just after entering the programmer mode. Thus, the PPAC can be incorporated as part of the initial interrogation when the external programmer is used for checking other pacemaker operating data. It is to be noted that while a PPAC of approximately 100 ms is long enough to get a good reading with just one such burst, redundant readings can be made to increase reliability, e.g., avoid a false positive.

Although the invention has been illustrated primarily in the context of an implantable cardiac pacemaker, it is to be understood that the burst technique of this invention is applicable to other medical device environments. For the preferred pacemaker system application, the invention provides a safe automated method of AC delivery and measurement. While in the preferred embodiment impedance magnitude is measured and utilized as the indicator parameter, the invention also embodies examining phase shift of the sensed signal, since phase may convey additional information concerning the state of the lead. Delivery of such PPAC bursts has been found to drive the system to a steady state, such that impedance measurements in accordance with this invention have shown an excellent correlation of the PPAC amplitude to standard continuous AC impedance magnitude measurement. Importantly, the use of this burst feature avoids the inducing of arrhythmias. We have evaluated fibrillation thresholds, for both atrial and ventricular fibrillation, comparing the PPAC technique of this invention with continuous AC impedance measurements. We have found that the fibrillation threshold for the PPAC is approximately an order of magnitude higher than for continuous AC. We have further found that 10 Hz seems to be most sensitive to changes in lead configurations, i.e., bipolar and unipolar ring to can configurations.

What is claimed is:

1. An implantable pacemaker system, comprising a pacemaker and a lead, the pacemaker having means for delivering pace pulses to a patient's heart through the lead and the pacemaker having means for sensing patient heart signals through the lead, the system having lead impedance means for obtaining a measure of a lead impedance, said lead impedance means further comprising a controllable burst generator for delivering to said lead an AC burst having a duration in a range of 50–125 ms and a limited current, and timing means for controlling the timing of said burst to follow a delivered pace pulse so that said burst is delivered substantially within a refractory period of the patient's heart following delivery of said pace pulse.

2. The system as described in claim 1, wherein said burst generator comprises constant current means for delivering a constant current AC signal, and current limiting means for limiting said constant current to about 30 microamps.

3. The system as described in claim 1, wherein said timing means comprises means for generating a timing signal to control said burst generator to deliver said burst within 10 ms of a delivered pace pulse.

4. The system as described in claim 1, wherein said timing means comprises limit means for limiting said burst duration to a value of about of 100 ms±10 ms.

5. The system as described in claim 1, further comprising external programming means for programming the controllable pulse generator to thereby control the delivery of a said AC burst.

6. The system as described in claim 1, wherein said lead impedance means further comprises response means for tracking lead impedance measurements and automatically initiating an appropriate pacemaker response upon detection of a decrease of lead impedance below a predetermined threshold.

7. The system as described in claim 1, comprising control means for controlling said burst generator to deliver a predetermined series of said AC bursts, each said burst being delivered in a predetermined time relationship to a just delivered pace pulse.

8. The system as described in claim 1, comprising internal test initiation means for automatically initiating an impedance test by periodically delivering a said AC burst.

9. The system as described in claim 1, wherein said lead is a bipolar lead, and said lead impedance means comprises impedance means for obtaining a measure of the impedance of said bipolar lead during a delivery of a said burst.

10. The system as described in claim 1, wherein said lead is a unipolar lead, and said lead impedance means comprises impedance means for obtaining a measure of the impedance of said unipolar lead during a delivery of a said burst.

11. A method of determining the impedance of a pacing lead in a pacemaker system, comprising the steps of:

delivering a stimulus pulse through said lead;

generating and delivering a constant current AC burst following delivery of said stimulus pulse, said generating including limiting said burst to a time duration of about 50–125 ms and limiting the peak-to-peak current of said burst to about 30 microamps, and measuring the voltage across said lead during delivery of said burst, thereby obtaining a measure of said lead impedance.

12. The method as described in claim 11, further comprising the step of using an external programmer to initiate generation and delivery of at least one said AC burst.

13. The method as described in claim 11, further comprising the steps of limiting said AC burst to about 100 ms duration, and delivering said burst during a refractory peroid of a patient's heart following delivery of a said stimulus pulse.

14. The method as described in claim 11, further comprising the step of initiating said burst so that it is delivered during the patient's cardiac refractory period following delivery of a said stimulus pulse.

15. The method as described in claim 11, further comprising the step of delivering said burst upon delivery of said stimulus pulse.

16. The method as described in claim 11, further comprising the step of delivering said burst at a timed interval following delivery of said stimulus pulse.

17. The method as described in claim 16, further comprising the step of timing said interval to a value within 0.1 to 10 ms.

* * * * *